United States Patent
Bozzarelli

(10) Patent No.: US 10,052,477 B2
(45) Date of Patent: Aug. 21, 2018

(54) PERINEAL PROBE FOR ASYMMETRIC TREATMENTS

(71) Applicant: BEACMED S.r.L., Portalbera (Pavia) (IT)

(72) Inventor: Pier Luigi Bozzarelli, Portalbera (IT)

(73) Assignee: BEACMED S.r.L., Portalbera (Pavia) (IT)

( * ) Notice: Subject to any disclaimer, the term of this patent is extended or adjusted under 35 U.S.C. 154(b) by 0 days.

(21) Appl. No.: 14/521,587

(22) Filed: Oct. 23, 2014

(65) Prior Publication Data
US 2016/0114154 A1    Apr. 28, 2016

(51) Int. Cl.
A61B 5/0492    (2006.01)
A61N 1/05      (2006.01)
A61N 1/36      (2006.01)

(52) U.S. Cl.
CPC ........ *A61N 1/0524* (2013.01); *A61N 1/36007* (2013.01)

(58) Field of Classification Search
CPC ...... A61N 1/05; A61N 1/0524; A61N 1/0514; A61N 1/36007; A61N 1/36; A61N 1/0512; A61B 5/04882; A61B 5/4337; A61B 5/0492; A61B 5/0488; A61B 5/00; A61F 2/00; A61F 2/0004
USPC ............................. 600/29, 546; 607/66, 116
See application file for complete search history.

(56) References Cited

U.S. PATENT DOCUMENTS

| | | | |
|---|---|---|---|
| 4,396,019 A * | 8/1983 | Perry, Jr. ....................... 600/546 |
| 5,662,699 A | 9/1997 | Hamedi et al. | |
| 6,692,490 B1 | 2/2004 | Edwards | |
| 9,622,678 B2 * | 4/2017 | Bozzarelli .......... A61N 1/36007 |
| 2004/0030360 A1 | 2/2004 | Eini et al. | |
| 2009/0222060 A1 | 9/2009 | Boyd et al. | |
| 2014/0088590 A1* | 3/2014 | Bozzarelli ............ A61N 1/0512 606/41 |

FOREIGN PATENT DOCUMENTS

| EP | 2759263 A1 * | 7/2014 |
| FR | 2 827 520 A1 | 1/2003 |
| GB | 2 284 991 A | 6/1995 |

OTHER PUBLICATIONS

The European Search Report for European Application No. EP 13 15 2342, two pages, completed Jun. 21, 2013.

* cited by examiner

*Primary Examiner* — Carl H Layno
*Assistant Examiner* — Jon Eric C Morales
(74) *Attorney, Agent, or Firm* — Vorys, Sater, Seymour & Pease LLP; Ari Zytcer

(57) ABSTRACT

Provided is a perineal probe for asymmetric treatments extending primarily along a longitudinal axis and including: a main rod extending primarily along the longitudinal axis; a plurality of electrodes, the perpendicular projection of which along said longitudinal axis is substantially in the same position, and reciprocally spaced in directions perpendicular to the longitudinal axis and connected to the main rod by means of deformable arms, and sensing means to detect the deformation of the arms.

7 Claims, 2 Drawing Sheets

PERINEAL PROBE FOR ASYMMETRIC TREATMENTS

FIELD OF THE INVENTION

The present invention relates to a perineal probe perineal probe, suitable to be inserted into the vaginal cavity and to detect electromyographic activity and to administer electrical stimulation for asymmetric treatments, which are treatments operating simultaneously and differentially on two sides of the treated body portion, said perineal probe extending primarily along a longitudinal axis.

DESCRIPTION OF THE PRIOR ART

In particular, the invention concerns a specific perineal rehabilitation device and a process for making said device.

Various methods and devices for the re-education of incontinence are currently known.

In particular, incontinence, especially female urinary incontinence, frequently results after lacerations of the pelvic muscles and cartilage due to trauma during childbirth.

Very often, the gynaecologist attending the birth intentionally cuts the pelvic floor muscles in a procedure known as episiotomy, to prevent spontaneous laceration and facilitate the birth. This is now a routine procedure carried out in about 80% of natural births and is usually performed in a mediolateral position.

Episiotomies however result in a marked asymmetry of the pelvic floor functioning of the puerpera.

Faecal or urinary incontinence may also be caused by other additional factors.

Current methods of re-education for the treatment of incontinence involve the use of vaginal or anal probes to detect electromyographic activity using EMG (electromyography) or to administer electrical stimulation, or to measure the pressure in the vaginal or anal cavity.

These probes are characterised by metal or metallised electrodes, with a circularly symmetric structure.

Some types permit the simultaneous measurement, by means of a latex membrane, of the pressure exerted by the pelvic floor muscles.

In particular a probe patented by this same applicant under patent IT-B-1358410, filed on 16 Feb. 2004, permits the sensing or asymmetric stimulation of the part of the body being treated.

In detail, the probe described in the aforesaid patent permits a differentiated bilateral treatment of the two branches, left and right (Lh and Rh), of the pubococcygeus muscle with the simultaneous measurement of the overall force exerted.

However, said probe is expensive and complex, particularly in terms of its production.

SUMMARY OF THE INVENTION

In this situation the technical purpose of the present invention is to devise a perineal probe for asymmetric treatments able to substantially overcome the drawbacks mentioned above.

Within the sphere of said technical purpose, an important purpose of the invention is to provide a process for making a perineal probe for asymmetric treatments that permits the differentiated treatment, in particular right-left (Rh-Lh), of the pubococcygeus muscle.

A further purpose of the invention is, thus, to design a reduced-cost process for making a perineal probe for asymmetric treatments.

The technical purpose and specific aims are achieved with a perineal probe suitable to be inserted into the vaginal cavity and to detect electromyographic activity and to administer electrical stimulation for asymmetric treatments, which are treatments operating simultaneously and differentially on two sides of the treated body portion, said perineal probe extending primarily along a longitudinal axis and comprising: a main rod extending primarily along the longitudinal axis; four electrodes the perpendicular projection of which along the longitudinal axis is substantially in the same position; the electrodes being reciprocally spaced in directions perpendicular to the longitudinal axis; a plurality of arms each one connected to the main rod and to only one of the electrodes.

BRIEF DESCRIPTION OF THE DRAWINGS

The characteristics and advantages of the invention are clearly evident from the following detailed description of a preferred embodiment thereof, with reference to the accompanying drawings, in which:

FIG. 5 is a front view of the perineal probe.

DESCRIPTION OF THE PREFERRED EMBODIMENTS

Figure 1:
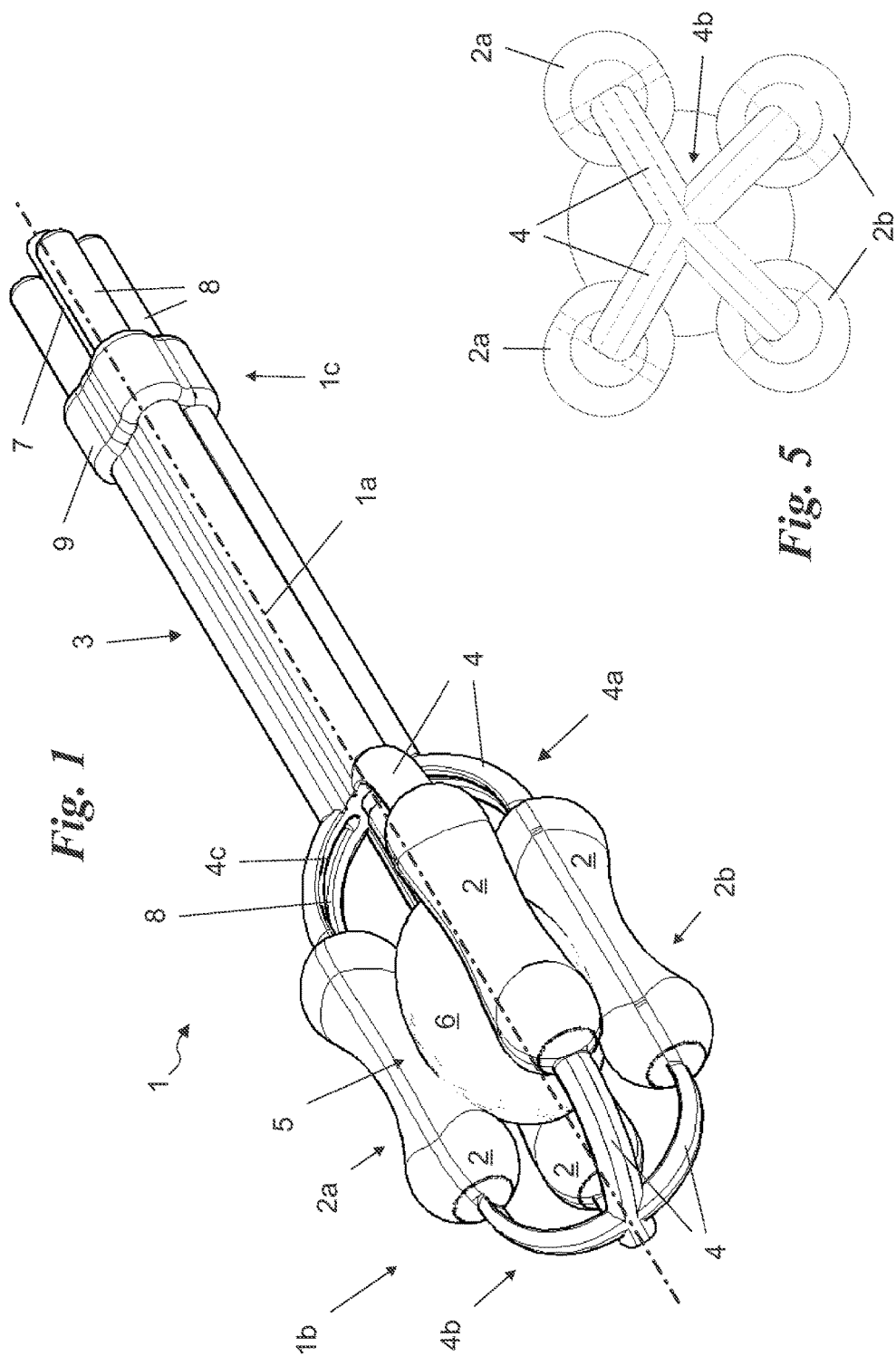
FIG. 1 is an axonometric view of the perineal probe according to the invention.
Figure 2:
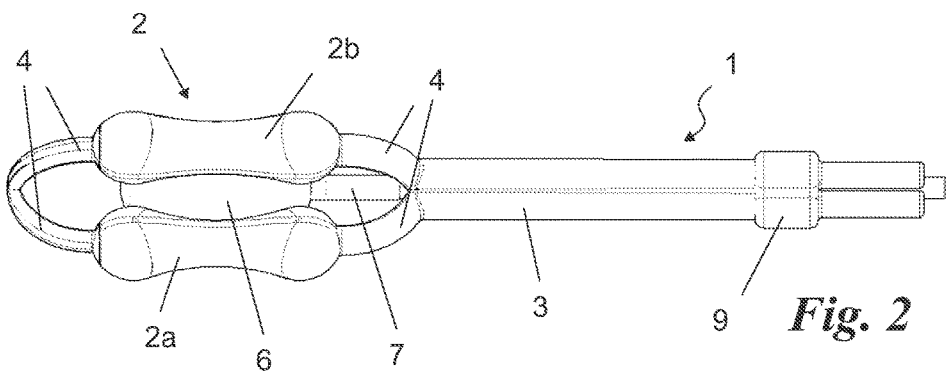
FIG. 2 is a side view of the perineal probe.
Figure 3:
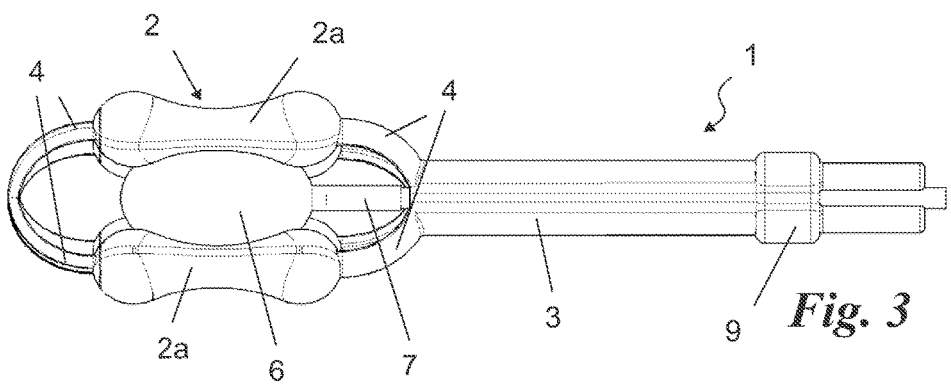
FIG. 3 is a view from the top of the perineal probe.
Figure 4:
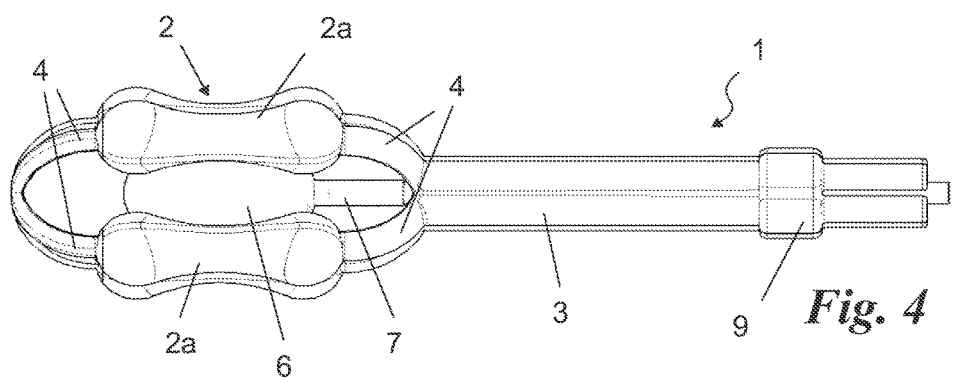
FIG. 4 is a view from the bottom of the perineal probe.

With reference to said drawings, reference numeral 1 globally denotes the perineal probe for asymmetric treatments according to the invention. It is suitable to be inserted into the vaginal cavity, and to be functionally connected to control means outside the probe 1 suitable to control or receive information from said probe, in particular to detect electromyographic activity using EMG (electromyography) and/or to administer electrical stimulation.

The perineal probe 1 extends primarily along a longitudinal axis 1a and comprises, in brief, a main rod 3 extending primarily along the longitudinal axis 1a, a plurality of electrodes 2 each of which is connected to the main rod 3 by means of a deformable arm 4 and sensing means 5 to detect the deformation of the arms 4.

More specifically, the main rod 3 is substantially stem-shaped and is preferably made of a flexible material, such as a polymer of the polycarbonate, polyethylene or polypropylene type or of an elastomeric or similar material, for example overmoulded on top of the electrical connections 8, as described in detail later on in this document.

The rod 3 is delimited by a proximal end 1b comprising the electrodes 2 and a distal end 1c, connected, preferably by means of various cables, to the control means, comprising an end cover 9, preferably larger in size than the remainder of the rod 1 and produced separately, as described in more detail later on in this document.

The electrodes 2 are arranged substantially in the same position along the longitudinal axis 1a, that is to say their perpendicular projections along the longitudinal axis 1a are substantially in the same position and constitute substantially coinciding segments. The electrodes 2 are also reciprocally spaced, so as not to be reciprocally contacting, in directions perpendicular to the longitudinal axis 1a. The electrodes 2 are saddle-shaped and preferably they extend along 360° across a central axis parallel to the longitudinal axis 1a. The electrodes 2 are preferably four in number and comprise two upper electrodes 2a and two lower electrodes 2b. Moreover, the upper electrodes 2a are preferably reciprocally spaced further apart with respect to the lower electrodes 2b, as illustrated in FIG. 5. The electrodes 2 preferably define a single circumference the centre of which lies on the longitudinal axis 1a.

Each of the electrodes 2 is star-shaped, in particular of a shape comprising a narrowest part in a central portion. The group of the electrodes 2 thus also forms a star-shape and provides a support for the muscular branches of the pubococcygeus.

They are made of a material having a conductive external surface and preferably also a conductive internal surface. In particular, they may be made of polymers with a metallised surface, such as ABS or various elastomers, or of conductive polymers, such as nanoparticle-loaded polymers, metal, sintered powder metal, moulded metal or other.

Each electrode 2 is connected to the main rod 3 by means of a deformable arm 4. In particular, the arms 4 are primarily deformable in a radial direction with respect to the longitudinal axis 1a.

The arms 4 thus have a main section of extension in a circumferential direction with respect to the circumference defined by said electrodes 2 with the centre along the axis 1a. They also have a shape that is preferably approximately semi-circular with the straight portion facing towards the axis 1a and having an opposite circumferential direction and curved portion. Along the internal straight portion of the arms there is also preferably a recess 4c, suitable to house an electrical connection 8, such as an electrical cable or a flexible printed circuit (FPC) or other connection.

The arms 4 are preferably present in correspondence with both the proximal end and the distal end, in a direction parallel to the longitudinal axis of the electrodes 2.

There are thus two substantially symmetrical groups of arms 4, a distal group 4a and a proximal group 4b. Preferably only the distal group 4b is provided with the recesses 4c.

The proximal group 4b terminates in correspondence with the proximal end 1b of the probe 1.

The arms 4 are preferably made of a polymer of the polycarbonate, polypropylene or polyethylene type or of an elastomeric material or other similar material. Preferably they are made of the same material as the rod 3 and formed in one piece therewith. Moreover, they are connected to the electrodes preferably by means of joints and possibly gaskets suitable to guarantee the fluid-tightness of said joints or even by means of conventional chemical bonding agents.

The sensing means 5 preferably comprise a balloon 6, appropriately inflatable and housed in the volume comprised between the electrodes 2.

The balloon 6 is preferably connected to the control means via a pneumatic hose 7. The latter is made of flexible and preferably substantially non-elastic material, and is suitable to deform in contrast to the deformations of the arms 4 and the subsequent movements of the electrodes 2 which alter the shape of the balloon, maintaining the value of the surface area constant. As a consequence, said variations in shape reduce or increase the internal volume of said balloon 6 so as to compress the fluid, air or liquid contained in the balloon. Said compression of the fluid inside the balloon is directly proportional to the radial deformation of the arms and thus directly proportional to the force exerted by the contraction of the pubococcygeus muscle.

The pneumatic hose is preferably housed at the centre of the rod 1, where there is a hole to house said pneumatic hose 7.

Alternatively, the pneumatic hose 7 may also be inserted outside the rod 3 and even after the probe 1 has been made.

The perineal probe 1 described above is manufactured by means of a process which first of all involves the production of the electrodes 2, the proximal group 4b of arms 4 and the central part of the rod 3.

Said elements are preferably made by means of moulding various polymeric materials. In particular, the rod 3 comprises hollow portions suitable to permit the insertion of the electrical connections 8.

The electrodes 2 are also metallised or made directly of metal.

The end cover 9 is instead preferably made by over-moulding various polymers on top of said electrical connections 8.

A next step consists of inserting the electrical connections 8 inside the rod 3. The electrical connections 8 are then inserted into the recesses 2c and may also be glued using an acrylic or similar adhesive.

The electrical cables 8 are thus connected electrically to the electrodes 2, preferably to the inside thereof, which are, in turn, connected to the external surface.

The electrodes 2 are fixed to the arms 4, possibly with the addition of cyanoacrylate adhesive or even a seal.

Lastly, the balloon 6 is inserted and the pneumatic hose 7 is preferably inserted into a specific hole in the centre of the rod 3 or on the outside thereof or, alternatively, the pneumatic hose 7 is also over-moulded with the electrical cables.

At the opposite end the hoses 7 and the connections 8 lead out of the rod 3 and of the end cover 9 and are connected via specific connections, preferably of a type that is known, to said means for controlling the probe 1.

The use of a perineal probe 1 according to the invention, described above in a structural sense, is as follows.

The probe 1 is connected, for use, to the control means. It is then electrically and pneumatically connected to the control means and can transmit electrical or mechanical impulses, by means of the sensing means 5, to the parts of the body into which it is inserted. Vice versa, the probe can transfer the electrical signals, caused by the muscular reactions, or mechanical signals, caused by the contraction of the area, coming from the parts of the human body, in particular from the perineal muscles, to the control means.

The control means are also able to detect which of the different electrodes or group of electrodes the impulses are coming from or which electrode to send them to.

If the part of the perineum affected by the presence of the electrodes contracts, the arms 4 bend, moving the electrodes 2 towards the longitudinal axis 1a and squeezing the balloon 6, which transmits the change in pressure of the fluid inside it to the control means.

The probe 1 according to the invention achieves some important advantages.

In particular, the probe 1 enables the advantageous implementation of asymmetric treatments or observations for the various parts of the body, in particular for the pubococcygeus muscle or pelvic floor.

In particular the possibility of performing a differentiated EMG measurement (Rh-Lh) and simultaneously measuring the overall strength, enables better diagnosis and more accurate planning of the therapy, as well as the objectification of the results achieved during the rehabilitation process.

The possibility of intervening differentially (right/left or even above/below) and simultaneously measuring the overall strength, represents a notable improvement in the possibility of success of the treatment.

In preventing urinary incontinence and during rehabilitation, the possibility of operating simultaneously and differentially on the two sides considerably improves the outcome of the treatment and also avoids the risk of bothersome over-stimulation of the area being treated.

Lastly, owing to its particular structure and the advantageous production process thereof, said probe 1 is very simple, robust and economical.

All the elements as described and claimed herein may be replaced with equivalent elements and the scope of the invention includes all other details, materials, shapes and dimensions as claimed in the independent claims.

The invention claimed is:

1. A perineal probe, configured to be inserted into the vaginal cavity and to detect electromyographic activity and to administer electrical stimulation for asymmetric treatments, which are treatments operating simultaneously and differentially on two sides of the treated body portion, said perineal probe extending primarily along a longitudinal axis and comprising:
    a main rod extending primarily along said longitudinal axis;
    four electrodes the perpendicular projection of which along said longitudinal axis is substantially in the same position;
    each one of said electrodes is saddle-shaped and extending along 360° across a central axis parallel to the longitudinal axis;
    each one of said electrodes having a circular extension in circumferential direction in respect to said longitudinal axis of a turn;
    said electrodes being reciprocally spaced in directions perpendicular to said longitudinal axis; and
    a plurality of arms being deformable and each one connected to said main rod and to only one of said electrodes,
wherein said electrodes define a single circumference the centre of which lies on said longitudinal axis.

2. The perineal probe as claimed in claim 1, comprising two upper electrodes and two lower electrodes, and wherein said upper electrodes are reciprocally spaced further apart with respect to said lower electrodes.

3. The perineal probe as claimed in claim 1, wherein said arms are deformable.

4. The perineal probe as claimed in claim 3, wherein said arms are deformable primarily in a radial direction with respect to said longitudinal axis.

5. The perineal probe as claimed in claim 3, comprising sensing means to detect the deformation of said arms.

6. The perineal probe as claimed in claim 5, wherein said sensing means comprise a balloon housed in the volume comprised between said electrodes.

7. The perineal probe as claimed in claim 6, wherein said sensing means comprise a pneumatic hose connected to said balloon and connectable to said control means of said perineal probe.

* * * * *